Figure 2A:
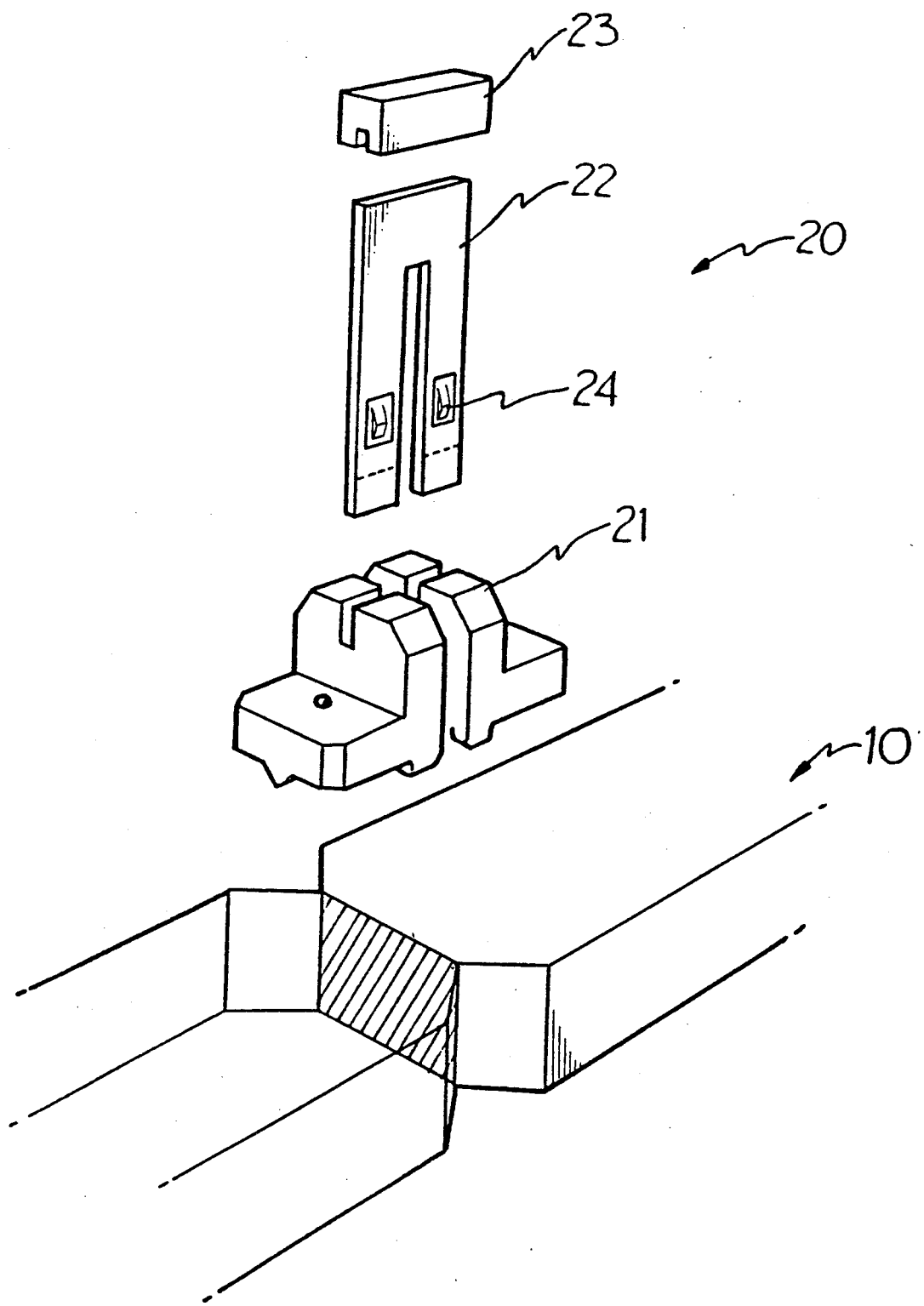

United States Patent [19]
Wycherley et al.

[11] Patent Number: 5,033,309
[45] Date of Patent: Jul. 23, 1991

[54] APPARATUS FOR MEASURING SHEAR STRESS AND STRAIN CHARACTERISTICS OF ADHESIVES

[75] Inventors: Graham W. Wycherley, Nunawading; Ivan Grabovac, East Rosanna, both of Australia

[73] Assignee: The Commonwealth of Australia, Australia

[21] Appl. No.: 437,090

[22] Filed: Nov. 16, 1989

[30] Foreign Application Priority Data
Nov. 18, 1988 [AU] Australia .............................. PJ1526

[51] Int. Cl.$^5$ .............................................. G01B 5/30
[52] U.S. Cl. ........................................ 73/842; 73/774
[58] Field of Search ............... 73/789, 841, 842, 845, 73/846, 849, 766, 774, 781, 775, 777–780, 760; 33/783, 787, 788, 789, 790

[56] References Cited
U.S. PATENT DOCUMENTS

| | | | |
|---|---|---|---|
| 3,184,962 | 5/1965 | Gay | 73/774 |
| 4,041,806 | 8/1977 | Klar | 73/789 |
| 4,856,342 | 8/1989 | Bottenbruch et al. | 73/827 |

FOREIGN PATENT DOCUMENTS
0855443 8/1981 U.S.S.R. ................................ 73/842

OTHER PUBLICATIONS
Krieger, "Stress Analysis Concepts for Adhesive Bonding of Aircraft Primary Structure", IMechE 1986.

Primary Examiner—Robert Raevis
Attorney, Agent, or Firm—Roylance, Abrams, Berdo & Goodman

[57] ABSTRACT

An apparatus and method of measuring the stress and strain characteristics of adhesives under uniform shear conditions. An Iosipescu sample (10) is used, in which at the shear line, the sample is joined by the adhesive to be tested. Pure shear is applied to the sample at the bond line and the distortion of the adhesive bond is measured. The apparatus (20) is attached to the specimen (10) by clamp means (30). The apparatus (20) comprises a fork means (22) and means to transmit the displacement (21) of the two parts of specimen (10) to the fork means (22) and means to measure the displacement, for example strain gauges attached to a Wheatstone bridge circuit. The specimen (10) with apparatus (20) attached is placed into a tensile testing machine especially adapted to receive the sample and apply shear to the adhesive bond line.

6 Claims, 7 Drawing Sheets

FIGURE.1
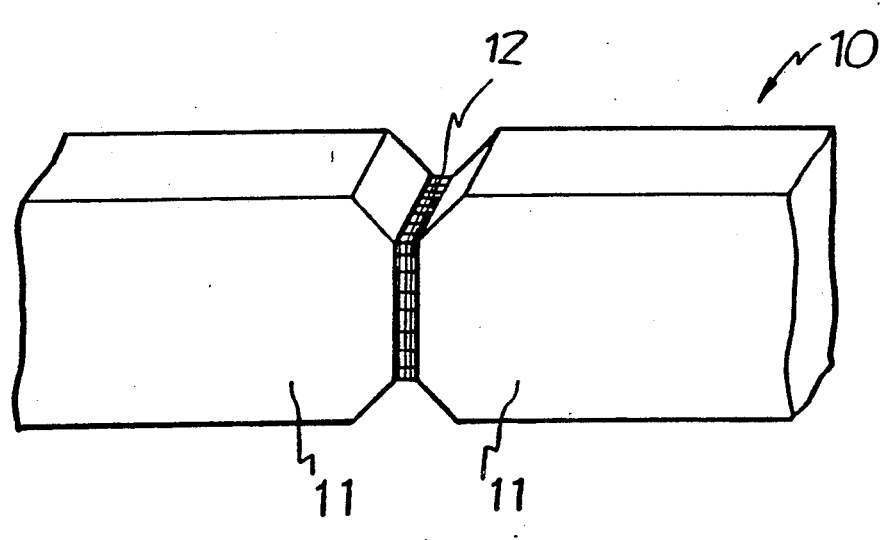
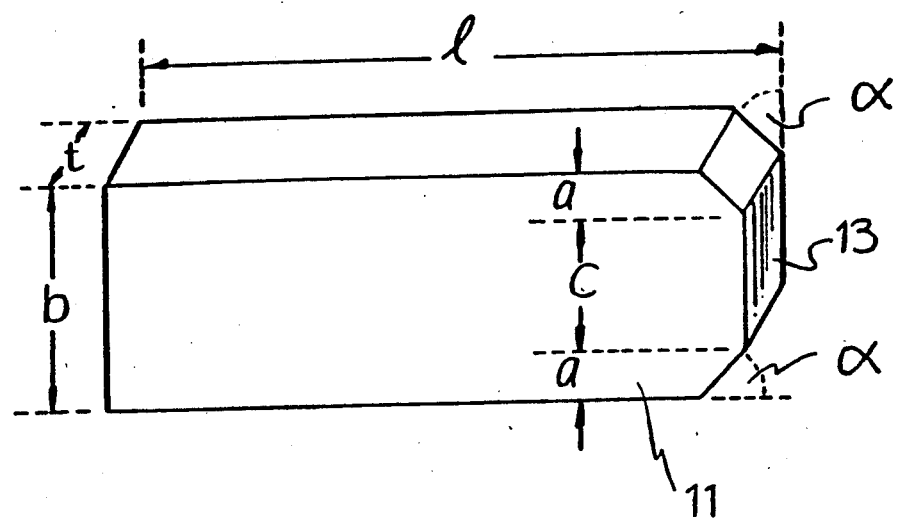
FIGURE.1A

APPARATUS FOR MEASURING SHEAR STRESS AND STRAIN CHARACTERISTICS OF ADHESIVES

This invention relates to a novel apparatus and method for measuring the stress and strain characters of adhesives under uniform shear conditions. The invention makes use of an Iosipescu sample wherein the adhesive to be tested is placed at the shear line of the sample as a join.

Recently significant development have resulted in adhesives and their use in adhesive bonding so that adhesive bonding is now widely used as a joining method for critical structural components, especially in aerospace applications.

To achieve the required reliability and safety margins, designers need data on the shear stress-strain behaviour of adhesives, particularly on properties such as shear modulus and elastic and plastic strain to failure. Such data are not easily obtained, partly because of the difficulties in measuring strain in a bond line which may be only 0.1 mm in thickness. Although a number of test configurations are in existence all have some disadvantages, ranging from cost and problems in specimen preparation to a questionable shear field in the region of interest.

Prior-art methods of testing the characteristics of adhesives include the "thick-adherend lap shear-type" method which is fully disclosed in "Stress analysis concepts for adhesive bonding of aircraft primary structure" R. B. KRIEGER, from the International Conference on Structural Adhesives in Engineering, Bristol, UK, 1986, p. 1. The method uses essentially a lap shear specimen constructed with thick adherends to minimize shear stress non-uniformity. To measure shear distortion of the adhesive bond line two sensors (i.e. LVDT coils) are used for which separate modules provide power excitation, signal averaging and recording. Also, since the adhesive shear stress is not entirely uniform across the test area, there are some doubts as to whether a maximum distortion of adhesive layer is obtained, and thus measured, for a given shear stress as a result of inherent adherends bending.

The ASTM method (Designation: E229-70 (Reapproved 1981)) measures the pure shear of adhesives by applying torsional shear forces to the adhesive through a circular specimen which produces a uniform stress distribution. The torsional shear forces are applied by a torsional shear jig without inducing bending, peeling, or transverse shear stresses in the bond line. The shear strain is measured with an ASTM Class A or Class B-1 extensometer, or alternatively an optical lever system is used. However, even though this method is reasonably accurate and gives direct results, specimen preparation is very time consuming and costly.

A much simpler method involves using strain gauges directly on the specimen per se, but this method is also costly, since the gauge, once attached to the specimen, can be used only once. Then after use is disposed of with the sample.

Therefore, in the light of the apparent problems with the prior art, the applicants have invented an apparatus which is reusable and inexpensive, and also simpler to use, producing more accurate and direct measurements of strain.

The present invention is predicated upon selection of the "Iosipescu" method (see N. Iosipescu, Journal of Materials, Vol. 2, No. 3, 1967, p 537). The test was originally developed for measuring the shear characteristics of metals and has in more recent years been extensively studied in relation to testing fibre-reinforced composites. These studies have amply demonstrated the uniformity of the shear stress across the sample. The Iosipescu method involves choosing a specimen which at the shear line, when a shearing force is applied thereto, exhibits shear in that direction only, thus giving a true value of shear.

The present invention adapts the Iosipescu method to measuring the shear characteristics of adhesives by dividing the normal Iosipescu specimen into two at the shear line and rejoining the two sections with the adhesive to be tested.

The invention provides an apparatus for measuring the extent of the shear distortion in adhesive bonds comprising means for applying a shear force to an Iosipescu-type specimen, having an adhesive bond line as the shear line and means for measuring the resultant distortion of the adhesive bond.

Preferably, the invention may provide an apparatus for measuring shear in adhesive bonds wherein the apparatus may comprise an elastic fork with two strips wherein said strips deflect as a result of a shearing force applied to the specimen, means for attaching said fork to an Iosipescu-type specimen having an adhesive bond line as the shear line and said strips having means to measure the strain attached thereto. More preferably, strain gauges may be attached to the elastic strips to measure the strain resulting from any shear force applied to the specimen. Further, the strain gauges may be attached to a Wheatstone bridge circuit to measure the strain. Circuit bridge excitation power, signal conditioning and recording may be provided by an existing internal circuitry of the tensile testing machine.

Preferably said means for applying a shear force to an Iosipescu-type specimen comprises a clamp means adapted to retain the Iosipescu-type specimen and a force applying means. The clamp means thus aids in retaining the sample in position and allow the shear force to be accurately applied to the adhesive bond line of Iosipescu sample.

Preferably the clamp means comprises at least two clamps which are adapted to fit onto either side of the bond line of the Iosipescu-type specimen and further, each of the clamps may be connected to the force applying means.

The force applying means is preferably a tensile testing machine and the clamps means may be adapted to fit into the existing recesses of the tensile testing machine.

The invention further provides a method of measuring the shear distortion in adhesive bonds comprising the steps of:

(a) preparing an Iosipescu-type specimen having an adhesive bond line of the adhesive to be tested as the shear line;

(b) applying a shear force to the Iosipescu-type specimen on its bond line; and (c) measuring the resultant distortion of the adhesive bond.

The method of the invention generally uses the apparatus as previous described.

Preferably, the resultant distortion of the adhesive bond is measured by an elastic fork with two strips wherein said strips deflect as a result of a shearing force applied to the specimen, means for attaching said fork to an Iosipescu-type specimen having an adhesive bond line as the shear line and said strips having means to measure the strain attached thereto. More preferably, strain gauges may be attached to the elastic strips to measure the strain resulting from any shear force applied to the specimen. Further, the strain gauges may be attached to a Wheatstone bridge circuit to measure the strain. Circuit bridge excitation power, signal conditioning and recording may be provided by an existing internal circuitry of the tensile testing machine.

Preferably said shear force is applied to an Iosipescu-type specimen comprises a clamp means adapted to retain the Iosipescu-type specimen and a force applying means. The clamp means thus aids in retaining the sample in position and allow the shear force to be accurately applied to the adhesive bond line of Iosipescu sample.

Preferably the clamp means comprises at least two clamps which are adapted to fit onto either side of the bond line of the Iosipescu-type specimen and further, each of the clamps may be connected to the force applying means.

The force applying means is preferably a tensile testing machine and the clamps means may be adapted to fit into the existing recesses of the tensile testing machine.

The nature of the invention will be more fully appreciated in the following preferred embodiment.

Figure 2B:
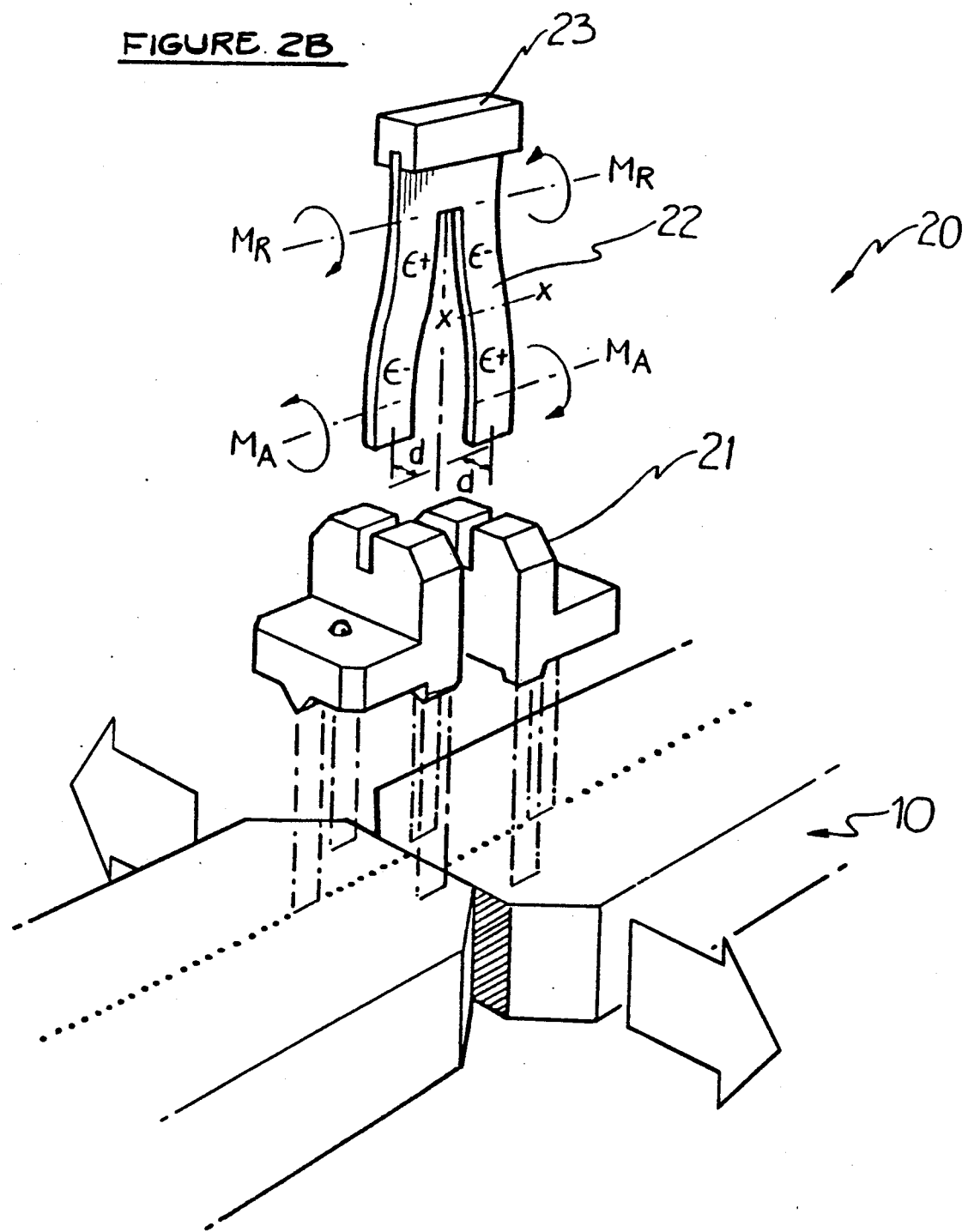
Figure 3:
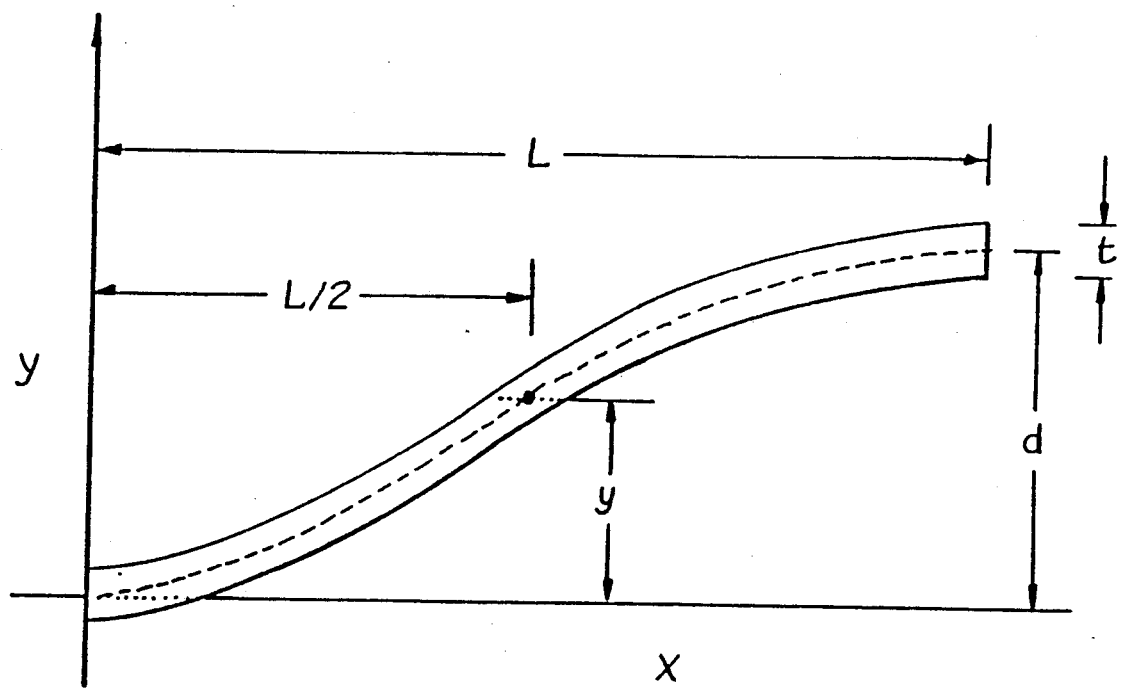
Figure 4:
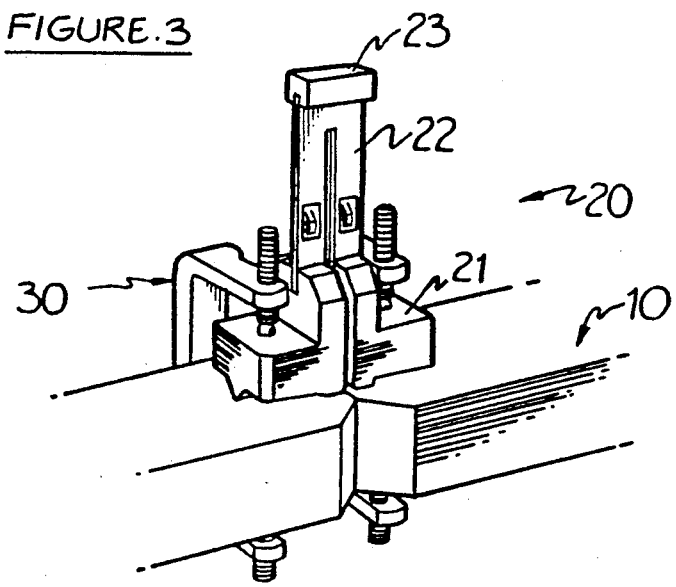
Figure 5:
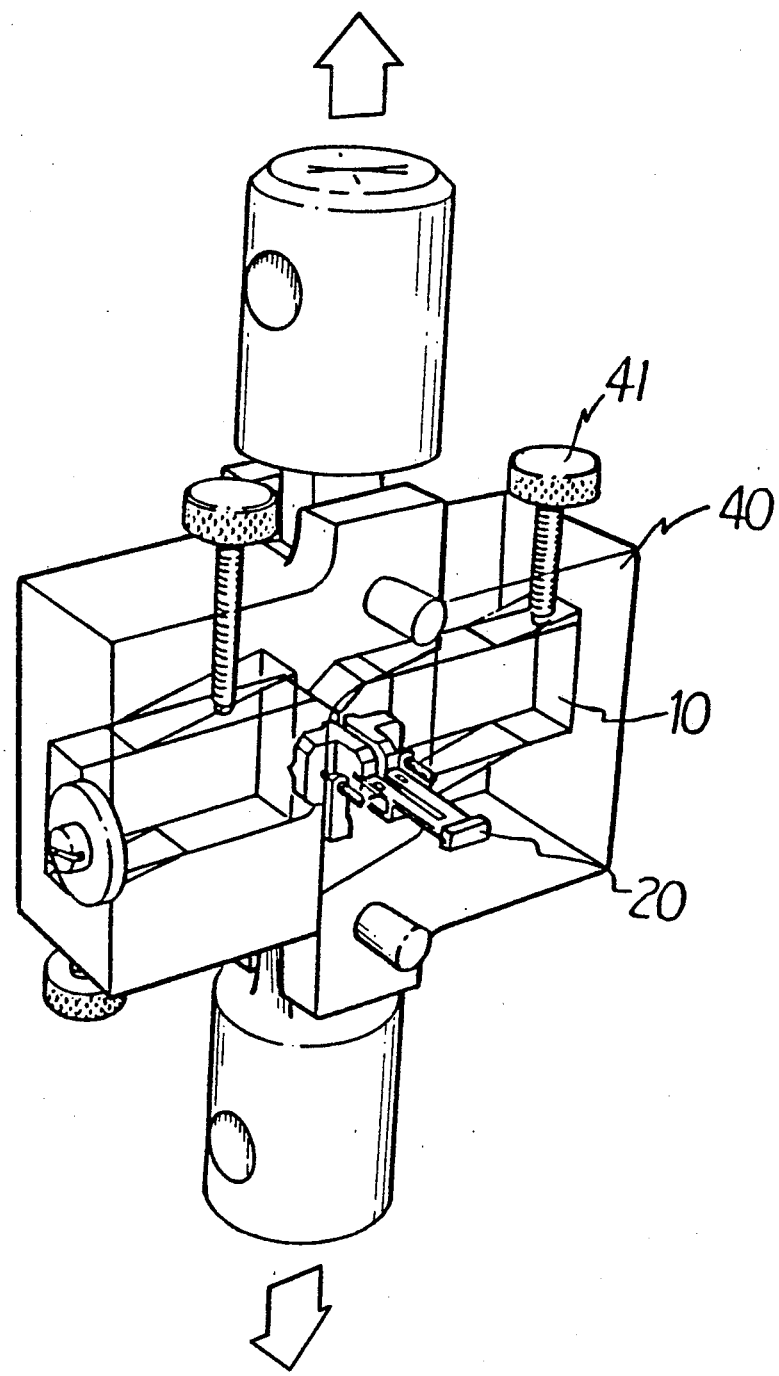
Figure 6:
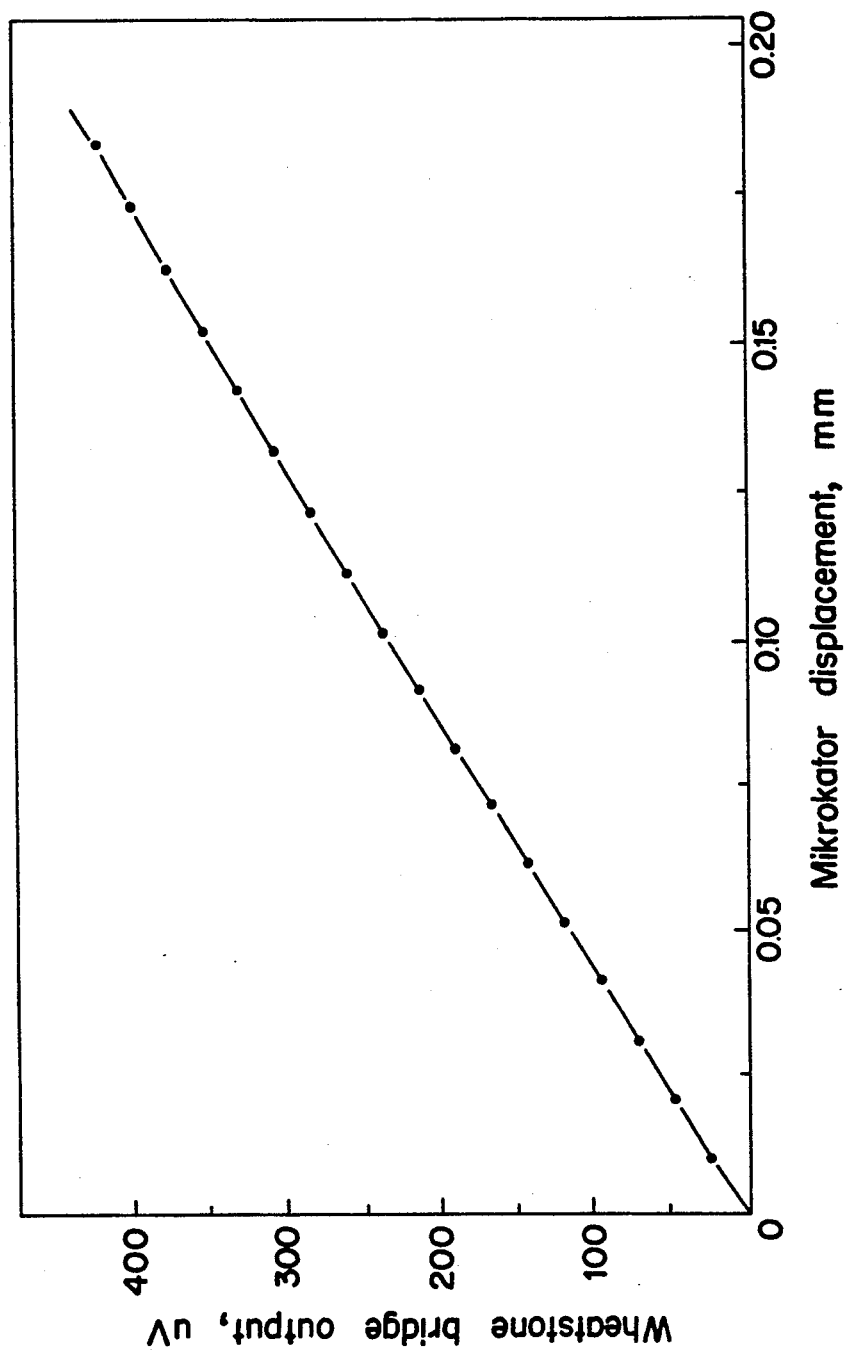
Figure 7:
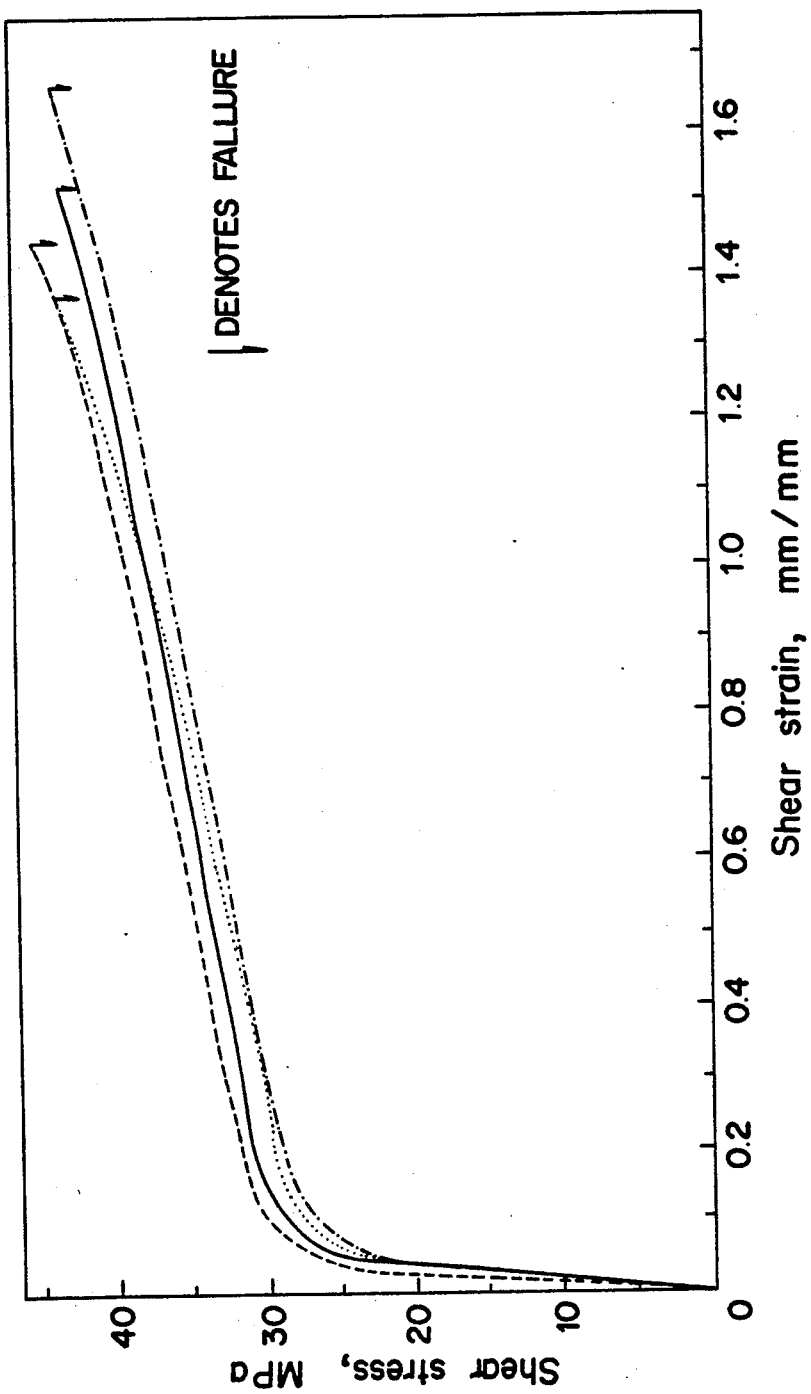

FIG. 1 is an example of an Iosipescu-type specimen.
FIG. 1a is an example of an adherend.
FIG. 2a is an embodiment of the apparatus of the invention with reference to the specimen.
FIG. 2b is an embodiment of the apparatus of the invention once a shearing force has been applied to the specimen.
FIG. 3 is a schematic drawing of a displaced elastic strip.
FIG. 4 is an embodiment of the apparatus of the invention attached to the specimen.
FIG. 5 is an embodiment of the apparatus of the invention attached to the specimen in tension grips.
FIG. 6 is an example of the calibration curve illustrating the relationship between Wheatstone bridge output ($\mu V$) and Mikrokator displacement (mm).
FIG. 7 is an example of a shear stress-strain curve of the expoxy-based film adhesive FM1000.

FIG. 1 discloses a schematic drawing of adhesively bonded Iosipescu-type specimen [10], in which two adherends [11] of the material to be joined are connected with the adhesive [12] on the bond area ([13] on FIG. 1a).

FIG. 1a discloses an adherend [11] wherein $\alpha$ is 45° to the bond area [13].

FIG. 2a illustrates a preferred embodiment (expanded view) of the apparatus of the invention [20].

The embodiment discloses three parts; means [21] to transmit the relative displacement of the adherends to the elastic strips of a two prong elastic fork [22] with sensing devices thereon [24] preferably strain gauges wherein each prong fits into the means for transmitting the relative displacement of the adherends [21] and means to support the elastic fork [23].

FIG. 2b shows the apparatus (expanded view) in the displacement mode. The adherends shear deflection is reproduced by the means [21] which transmit the relative deplacement of the adherends [10] to the elastic strips [22] thus for a given individual displacement (d) each strip experiences end applied moment ($M_A$). As a result of the opposing applied moments the elastic strips of the fork are subjected to bending giving rise to surface compressive and tensile strains (i.e. two$-\epsilon$ and two$+\epsilon$ respectively) away from the plane of inflection (x-x).

The slotted bar [23] interference fitted onto the other end of the fork [22] assists in balancing counteracting reactive moments ($M_R$) of opposing direction.

Preferably, to each side of the two elastic strips of the fork a small uniaxial strain gage is adhesively bonded (close to the sample end of the strips) and wired to form a Wheatstone bridge circuit. This forms the sensing means [24], as illustrated, from which the strain values are recorded.

The problem of determining the actual site of strain gauge attachment has been resolved by a combination of a theoretical and experimental approach. Theoretically, it could be shown that the magnitude of the surface compressive or tensile strain along the strip's free length and its dependence on that length can be related to a single beam theory. The illustration, (FIG. 3) showing one elastic strip (side view), is analogous to a beam member constrained at both ends, for which it is known that the case is governed by $$\frac{d^4y}{dx^4} = 0 \qquad (i)$$

where y is displacement and x is distance along the beam from either constrained end. Also from FIG. 3

$y=0$ for $x=0$ $y=d$ for $x=L$ and $\frac{dy}{dx} = 0$ for $x = 0$ and $x = L$ where d is the total end displacement and L is the free length. Solving equation (i) with these conditions gives $$y = \frac{3d}{L^2} x^2 \left[ 1 - \frac{2x}{3L} \right] \qquad (ii)$$

However, surface strain (tensile) is given by $$\epsilon = \frac{t}{2R}$$

where t is beam thickness and $$\frac{1}{R} = \frac{d^2y}{dx^2}$$

is the curvature at any point along the beam. Therefore using equation (ii) and solving gives $$\epsilon = \frac{3dt}{L^2} \left[ 1 - \frac{2x}{L} \right] \qquad (iii)$$

which indicates that strain at the half-length of the beam ($x=L/2$, point of inflection) vanishes and increases along the beam reaching a maximum at either end (i.e. $x=0$ or $x=L$) thus reducing equation (iii) to $$|\epsilon|_{max} = \frac{3dt}{L^2} \qquad \text{(iv)}$$

Note also, from equation (iv), that for a given displacement (d) strain is increased by decreasing beam length (L).

From the above it is shown that if the strain gauges are to be usefully employed, their position should be close to an end of an appropriately short elastic strip. Their equally distant positions from the chosen end will also ensure that the circuit bridge is temperature compensated and that the magnitude of the compressive and/or tensile strains, seen by the strain gauges attached to these sites, are comparable.

The experimental part of this approach was concerned with implementing the above findings. This entails optimizing the strips' length and positioning the strain gauges so that the circuit bridge produced largest output signal (i.e. highest strain) for a minimal displacement with signal linearity over the entire measuring range.

FIG. 4 illustrates the preferred embodiment of the apparatus [20] as attached to the specimen [10]. The apparatus [20] is attached to the sample in this preferred embodiment with G-type clamps [30]. A positioning device (not shown) can be used to align the apparatus symmetrically over the adhesive bond line.

FIG. 5 illustrates the specimen [10] with an attached apparatus [20] in grips [40] suitable for tensile loading and adapted to fit into a tensile testing machine. The specimen is kept in place by securing screws [41] being previously aligned by a positioning device (not shown) to ensure that the bond line is properly aligned. To this fixed arrangement the shearing force is applied in the direction of the arrows shown by the tensile testing machine.

In practice, the specimen final dimensions correspond to the Iosipescu data set out in the journal article by N. Iosipescu. A preferred adherend may have the following dimensions (depending on the tensile strength testing machine and grips etc.), FIG. 1A l = 50 mm
t = 10 mm
b = 20 mm
a = 4 mm
c = 12 mm
α = 45°

No lateral notches are considered necessary as suggested in the Iosipescu journal. Adherends can be re-used several times by remachining after each test if they cannot be cleaned by simple chemical means. This remachining process by which a fraction of a millimeter is taken off the bonding surface and notch faces is considered acceptable since there is no evidence of permanent set due to repeated application of the loads reached during the testing of the adhesive.

The bonding step is the most critical of the testing procedure. Adherends must be axially aligned before, during and after bonding to ensure bond line thickness uniformity and to allow the accurate measurement of the bond line thickness. The bonding pressure to the adherends must be accurate and constant while the adherends are being bonded. Ideally, a calibrated screw-operated spring clamp which encloses the specimen can be used to retain the specimen axially aligned and place a constant pressure to the specimen.

The bonding surface of the adherend is pretreated in a conventional way, for example, when epoxy film adhesives are being tested, the bonding surface of the aluminium adherend is first subjected to a standard surface pretreatment (i.e. vapour degrease and chromic acid etch). The cure is performed in a temperature controlled, air circulating oven. Specimens temperature near the bond line is monitored by a thermocouple inserted through the wall of the bonding assembly.

The bond line thickness must be measured in order to obtain meaningful and reliable shear data from the shear stress-strain curve. The selected technique involves measurement of the end-to-end distance of the adherend pair before and after bonding, thus giving the bond line thickness by difference. These measurements are performed by the use of a commercially available comparator equipped with a high resolution Mikrokator. Using the Mirkokator, reliable and reproducible bond line thickness measurements with an accuracy of $2.5 \times 10^{-3}$ mm can easily be achieved. In practice, handling of aluminium adherends should be minimized to maintain dimensional stability.

Prior to testing, the apparatus of the invention must be calibrated so in order to determine the relationship between the displacement of the strips and the Wheatstone bridge output.

Thus the strips are displaced and the distance measured and the corresponding Wheatstone bridge output is recorded.

For calibration purposes the Wheatstone bridge was operated at 1.03 V supplied by a Strain Gauge Meter model RD-203, manufactured by Applied Measurements, Australia and the output read from a Keithley 177 uV, digital multimeter. The resulting calibration curve, representative of any part of shearometer's measuring range of about 0.5 mm, is shown in FIG. 6. The typical sensitivity is 2.3 uV/um.

The apparatus is then attached to the specimen as illustrated in FIG. 4 and aligned onto the specimen to ensure that it lies symmetrically over the adhesive bond line.

The specimen with the apparatus attached thereto is then placed in the test grips suitable for tensile loading. Once again the specimen is aligned to ensure that the bond line is in the line of shearing forces.

The specimen is now ready for shear testing.

During actual shear testing the adhesive bond is continuously deformed as one adherend is moved with respect to the other at a preselected speed. One half of the attached apparatus reproduces this movement and as it does so the Wheatstone bridge becomes unbalanced due to the change in resistance of a stretched strain gauge foil. The recorded bridge output voltage is, hence, taken as being equivalent to a combined strain on adhesive and adherends. The contribution of the adherends is subtracted from above by evaluating their elastic deformation under identical test conditions using an identically shaped non-bonded specimen.

An example of the data and its reproducibility obtainable from this method is shown in FIG. 7. This gives the shear stress-strain curve of the epoxy-based film adhesive FM1000, which has been extensively used in the aircraft industry for many years, especially in such applications as helicopter rotor blades. From the initial, linear part of the curve the shear modulus can be determined: the rest of the curve provides information on the adhesive's elastic limit and strain to failure as well as the shear failure stress.

The application of the Iosipescu shear test as adapted for the determination of properties of structural adhesives under conditions of uniform shear has been described. This invention is an inexpensive, reusable and highly sensitive instrument that gives reproducible results. As a whole, it has been shown that the apparatus and method of using thereof enables determination of the complete adhesive stress-strain behaviour and thus evaluation of shear modulus, elastic and plastic strain to failure and the ultimate shear stress.

The claims defining the invention are as follows:

1. An apparatus for measuring the extent of the shear distortion in adhesive bonds comprising:
   (a) means for applying a shear force to an Iosipescu-type specimen, having an adhesive bond line as the shear line; and
   (b) means for measuring the resultant distortion of the adhesive bond including
      (i) an elastic fork with two strips wherein said strips deflect as a result of a shearing force applied to the specimen, each strip each having attached thereto means for measuring the strain, and
      (ii) means for attaching said fork to the specimen.

2. The apparatus of claim 1, wherein said means for applying a shear force to an Iosipescu-type specimen comprises:
   (i) a clamp means adapted to retain the Iosipescu-type specimen;
   (ii) a force applying means.

3. The apparatus of claim 2, wherein said clamp means comprises at least two clamps which are adapted to fit onto either side of the bond line of the Iosipescu-type specimen and each of said clamps is connected to the force applying means.

4. Method of testing and measuring the shear distortion in adhesive bonds comprising the steps of:
   (a) preparing an Iosipescu-type specimen comprising two adherends and having an adhesive bond line of the adhesive to be tested as the shear line;
   (b) measuring the thickness of the adhesive bond line;
   (c) applying a shear force to the adhesive bond line by moving one adherend of the Iosipescu-type specimen relative to the other adherend;
   (d) measuring the displacement of one adherend relative to the other and hence the resultant distortion of the adhesive bond, wherein the resultant distortion of the adhesive bond is measured by
      (i) an elastic fork with two strips wherein said strips deflect as a result of a shearing force applied to the specimen and each strip each having attached thereto means for measuring the strain; and
      (ii) means for attaching said fork to the specimen; and
   (e) using shear force and displacement measurements of steps (c) and (d) and the physical characteristics of the Iosipescu-type specimen to calculate shear stress and shear strain values of the adhesive.

5. The method of claim 4, wherein a shear force is applied to the Iosipescu-type specimen by:
   (i) a clamp means adapted to retain the Iosipescu-type specimen; and
   (ii) a force applying means.

6. The method of claim 5, wherein said clamp means comprises at least two clamps which are adapted to fit onto either side of the bond line of the Iosipescu-type specimen and each of said clamps is connected to the force applying means.

* * * * *